United States Patent [19]
Liebermann

[11] Patent Number: 5,400,015
[45] Date of Patent: Mar. 21, 1995

[54] FILTER CIRCUIT FOR A GASEOUS LEAK DETECTOR

[75] Inventor: Leonard N. Liebermann, La Jolla, Calif.

[73] Assignee: TIF Instruments, Inc., Miami, Fla.

[21] Appl. No.: 190,314

[22] Filed: Feb. 2, 1994

[51] Int. Cl.⁶ .............................................. G08B 17/10
[52] U.S. Cl. .................................... 340/632; 324/455
[58] Field of Search ....................... 340/632, 633, 634; 324/455; 73/23.31

[56] References Cited

U.S. PATENT DOCUMENTS

| | | | |
|---|---|---|---|
| Re. 32,552 | 6/1987 | Liebermann et al. | 340/632 |
| 4,228,429 | 10/1980 | Tsuchiya et al. | 340/362 |
| 4,766,763 | 8/1988 | Kurtz | 73/49.2 |
| 4,831,332 | 5/1989 | Rudisill et al. | 324/455 |
| 5,264,833 | 11/1993 | Jeffers et al. | 340/362 |

Primary Examiner—Jeffery A. Hofsass
Assistant Examiner—Julie Lieu

[57] ABSTRACT

A circuit improvement and method leading to increased leak detection sensitivity is provided for gaseous leak detectors which utilize a hand held probe. The circuit modification provides a high pass filter and additional circuit gain which are switched together in or out of the detection circuit. When the modification is switched in circuit it is necessary to move the probe with a sweeping motion while searching for a gaseous leak.

2 Claims, 1 Drawing Sheet

FILTER CIRCUIT FOR A GASEOUS LEAK DETECTOR

FIELD OF THE PRESENT INVENTION

This invention relates to a filter circuit for improving the detection capability of apparatus for finding gaseous leaks into the ambient atmosphere.

BACKGROUND OF THE INVENTION

Various commercial leak detectors are available for detecting gaseous leaks into the ambient atmosphere. As an example a leak detector for detecting refrigerant gas disclosed in U.S. Pat. No. Re 32,552 to Liebermann et al (1987) is incorporated herein for reference. Leak detectors are typically provided with a hand-held probe in order to search for leaks in pipe joints, crevices, and other localized regions. The usual procedure for finding a leak involves two phases: "search" and "verification". In the search phase the probe is scanned or wiped over suspected regions; the probe is moved with reasonably constant motion in search of an indication. During verification the motion is substantially stopped with an attempt to hold the probe directly on the leak for verification and pinpointing its location. Some leak detectors provide an indication of leak size during verification.

The type of gas sensor employed depends on the gas to be detected. As an example some employ the corona apparatus for detecting halogen gas leaks in refrigerant systems. When 1500 to 2000 volts are applied to the fine wire a corona discharge current occurs between the wire and an outside shell which diminishes when trace amounts of halogen gas enters the shell. Another type of gaseous leak detector employs a heated metal oxide sensor whose resistance changes when detecting natural gas. Still another refrigerant leak detector utilizes a heated platinum electrode to form a positive ion current; the ion current between the hot electrode and an outside shell increases in the presence of traces of halogen gas.

In these leak detectors electrical changes in the sensor caused by the presence of the leaking gas in the ambient atmosphere are monitored by circuitry to provide a signal of a leak. Typically, a visual and/or acoustical alarm is incorporated which is actuated by the electrical signal from the sensor.

These leak detectors have two noteworthy features in common: 1) They are subject to false signals or noise arising from local environmental variations. For example the corona sensor for refrigerant will respond to local humidity variations; the heated diode refrigerant sensor is sensitive to smoke; the metal oxide natural gas sensor will detect local thermal variations. 2) The alarm circuitry of each of these leak detectors is substantially direct coupled to the sensor to provide a constant alarm signal when the probe is held steady on a leak and the sensor yields a constant signal. This provision is required to properly use the verification procedure.

By using direct coupled circuitry solely, without filtering, present leak detectors have failed to exploit their maximum detection capabilities. Although filtering or signal processing in the detection circuitry can improve detection by selectively enhancing the signal and by diminishing the effect of environmental noise sources, none of these leak detectors incorporates such circuitry.

SUMMARY OF THE INVENTION WITH OBJECTS

A general object of the present invention is to improve the detection capabilities of gaseous leak detectors by making these devices more sensitive and thus able to detect smaller leaks and find leaks more rapidly.

Another general object of the present invention is to recognize that the optimum detection circuitry for the search and verification phases of leak detection is different for each phase, and to provide the optimum circuitry for each.

A more specific object of the present invention is to provide a high pass filter and means for additional gain which can be inserted in the conventional detection circuitry.

Another specific object is to provide switching circuitry for selecting two alternative detection circuits: The conventional circuitry with said high pass filter and additional gain, or the unmodified conventional circuit. Accordingly, "scan mode" is herein defined whenever the high pass filter and added gain are in circuit; "normal mode" is the alternative.

In accordance with the principles of this invention the scan mode decreases noise and false signals arising from local variations of the ambient atmosphere compared to the normal mode. These ambient variations are generally very slow, leading to low frequency electrical changes in the sensor. For example, in searching for halogen refrigerant leaks with the corona-type leak detector, local humidity variations result in slow corona current variations, often causing false signals. However these slowly varying interfering signals will be attenuated whenever the high-pass filter of this invention is inserted in circuitry. As a result of the noise reduction, increased gain of the circuitry can be used effectively without increasing false signals. Accordingly, higher gain accompanies the use of the high pass filter in this invention.

Further in accordance with this invention during the search phase of leak detection the probe is scanned over a leak. The signal generated during scanning will be pulse-like, as the moving probe approaches and then leaves the leak. A pulsed signal will pass unattenuated by a properly designed high pass filter. Furthermore the higher gain accompanying the filter will provide for increased pulse amplitude and improved detection. The overall improvement provided by the filter-gain combination is twofold: The filter reduces "noise", and added circuit gain increases the amplitude of the unattenuated pulse.

The normal mode in which the high-pass filter (and gain increase) is switched out of circuit, is still required for the verification phase of leak detection. If the probe is held stationary on the leak while in the scan mode, the signal will rapidly vanish, making verifications and pinpointing difficult. Accordingly it is intended that switching between the normal and scan modes of operation will be employed during leak detection when using this invention.

These and other objects, advantages, aspects, and features of the present invention will be more fully understood and appreciated upon consideration of the following detailed description of a preferred embodiment, presented in conjunction with accompanying drawings.

DETAILED DESCRIPTION OF A PREFERRED EMBODIMENT

Figure 1:
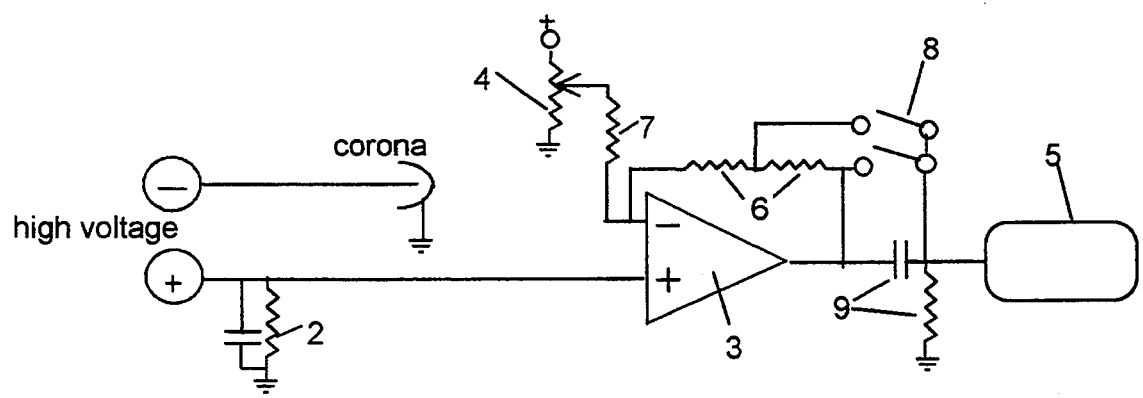
FIG. 1 is a schematic of circuitry illustrating the application of the invention utilizing the corona type halogen leak detector sensor.

To illustrate the details of the application of this invention a leak detector circuit is shown in FIG. 1. The detector is designed to find leaks in a halogen refrigeration system and employs the corona sensor. A high voltage source, pulsing or steady, of 1500 to 2000 volts generates a corona surrounding a fine wire located within the sensor at the tip of the probe. The sensor diameter is small, of the order of 5/16 in. so that it can probe close to the leak. In the presence of halogen gas the continuous corona current diminishes, compared to its value in the pure ambient atmosphere. The corona current generates a positive D.C. voltage in resistor 2 which is monitored by the operational amplifier 3.

The adjustment potentiometer 4 permits the inputs to amplifier 3 to be nulled when the sensor is operated in pure ambient atmosphere. Hence an output signal obtains only when a halogen leak is approached. The alarm 5 can be a light or sound source or both in combination.

The amplifier gain is controlled by the negative feedback resistors 6 and 7. In accordance with this invention the gain can be selectively increased by switching means 8.

Similarly a high pass filter consisting of the R-C combination 9 can also be inserted by switching means 8 into the input to alarm 5. The filter is preferably designed to pass frequencies greater than 0.5 Hz. Accordingly, disturbing "noise" resulting from ambient contaminants and corona current variations are considerably attenuated because they usually generate slowly varying signals below the pass band of the filter. Hence the amplifier gain can now be increased without increased false alarms.

Figure 2:
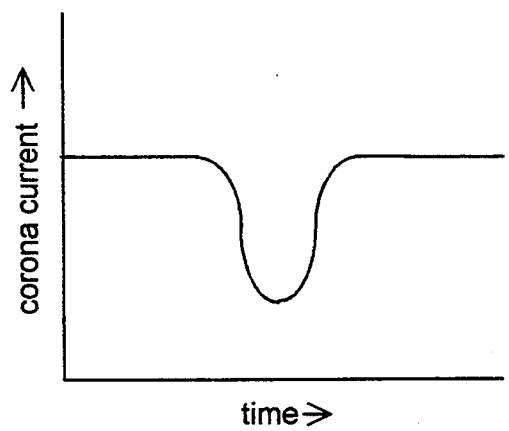
FIG. 2 represents schematically the output of the corona sensor when the probe is scanned past a leak.

FIG. 2 shows schematically the corona current decrease produced whenever the probe is scanned past a leak. Accordingly this will result in a voltage pulse in the signal circuitry. In accordance with this invention, this pulse will be unattenuated by the high pass filter and lead to a detection signal. However if the probe is held steadily on a Leak, the corona current will remain steadily lower; the steady signal will be attenuated by the filter and no detection will then be observed.

Upon detecting the region of the leak it is preferable to use switch 8 to revert to the normal unfiltered, lower gain circuit. The leak can then be located with pinpoint accuracy by steadily holding the probe on the leak source with the aid of the essentially steady detection signal.

To those skilled in the art to which the present invention pertains, many widely differing embodiments will be suggested without departing from the spirit and scope of the present invention. The descriptions and disclosures are intended solely for illustration and should not be construed as limiting the scope of the invention which is more particularly pointed out by the following claims.

What is claimed is:

1. A gaseous leak detector with a hand-held probe wherein an electrical signal is generated in relationship to the concentration of the gaseous impurity in the ambient atmosphere, including, a high-pass filter which a selectively inserted into or removed from a detection circuit by a switch, whereby sustained and slowly varying signals are attenuated only when said filter is inserted, and means for selectively increasing the gain of said detection circuit whenever said filter is inserted.

2. A method of improving the detection capability of a gaseous leak detector with hand held probe, wherein an electrical signal is generated in relationship to the concentration of a gaseous impurity in the ambient atmosphere, comprising the steps of:

providing a high pass filter which can be inserted into or removed from a detection circuit, whereby sustained and slowly varying signals are attenuated only when said filter is inserted, providing increased gain which can be added or removed in said detection circuit, providing a switch for selectively inserting or removing said high pass filter together with said increased gain in said detection circuit.

* * * * *